United States Patent [19]

Abe et al.

[11] Patent Number: 5,444,099

[45] Date of Patent: Aug. 22, 1995

[54] TERTIARY AMINOALCOHOL ANE PROCESS FOR PRODUCING THE SAME, AND, POLYURETHANE AND PROCESS FOR PRODUCING THE SAME

[75] Inventors: Hiroshi Abe, Albany, Calif.; Tetsuaki Fukushima, Wakayama, Japan; Kohshiro Sotoya, Wakayama, Japan; Shoichiro Harada, Wakayama, Japan; Hiroshi Kitagawa, Wakayama, Japan; Masayoshi Morii, Ibaraki, Japan; Yasutoshi Isayama, Wakayama, Japan

[73] Assignee: Kao Corporation, Tokyo, Japan

[21] Appl. No.: 123,165

[22] Filed: Sep. 20, 1993

Related U.S. Application Data

[62] Division of Ser. No. 845,594, Mar. 4, 1992, Pat. No. 5,315,041.

[30] Foreign Application Priority Data

Mar. 5, 1991 [JP] Japan .................. 3-38574
Mar. 8, 1991 [JP] Japan .................. 3-43849
Feb. 19, 1992 [JP] Japan .................. 4-32014

[51] Int. Cl.⁶ .................. C07C 215/02; C08G 18/14
[52] U.S. Cl. .................. 521/129; 521/164; 521/167; 521/174; 528/52; 528/65; 528/66; 528/78; 528/85; 564/471; 564/480; 564/504; 564/505; 564/507
[58] Field of Search .................. 528/78, 85, 52, 65, 528/66; 521/129, 164, 167, 174; 564/506, 471, 480, 504, 505, 507

[56] References Cited

U.S. PATENT DOCUMENTS 4,101,462 7/1978 Cuscurida et al. .

FOREIGN PATENT DOCUMENTS 668477 12/1965 Belgium .
0376602 7/1990 European Pat. Off. .
51-75795 6/1976 Japan .................. 521/167
63-265909 11/1988 Japan .
2075531 11/1981 United Kingdom .................. 521/164

Primary Examiner—Joseph L. Schofer
Assistant Examiner—John M. Cooney, Jr.
Attorney, Agent, or Firm—Birch, Stewart, Kolasch & Birch

[57] ABSTRACT

A tertiary aminoalcohol having a tert-amino group(s) in the main chain and hydroxyl groups at the terminals. The use of this compound for purposes different from that of ordinary amines and amine derivatives is expected.

A process for producing the tertiary aminoalcohol wherein a catalyst comprising copper, a transition metal element of the fourth period and a platinum group element of the group VIII, and further optionally containing an alkali metal or an alkaline earth metal is used.

A process for producing polyurethane using the above-mentioned tertiary aminoalcohol which can solve the problems occurring in the production of a polyurethane using a tertiary amine which has a strong irritating odor and is highly irritant to the skin as a catalyst, for example, deteriorations of working atmosphere and sales appeal of the polyurethane.

The chemical structure of the above-described tertiary aminoalcohol is as follows:

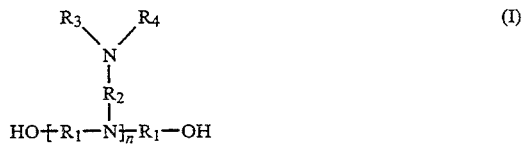

20 Claims, 2 Drawing Sheets

FIG. 1A
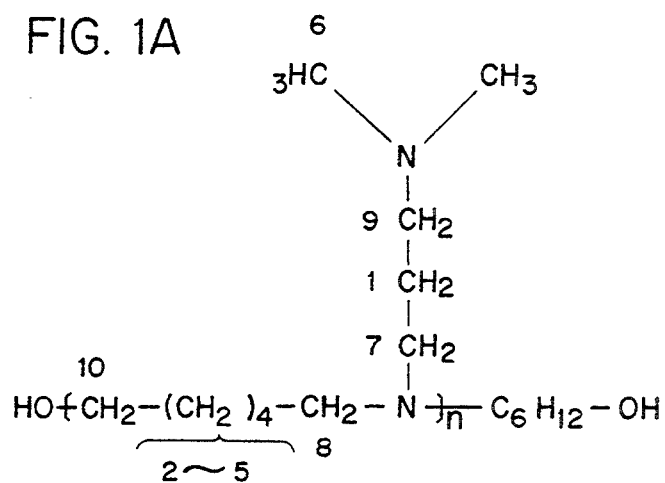
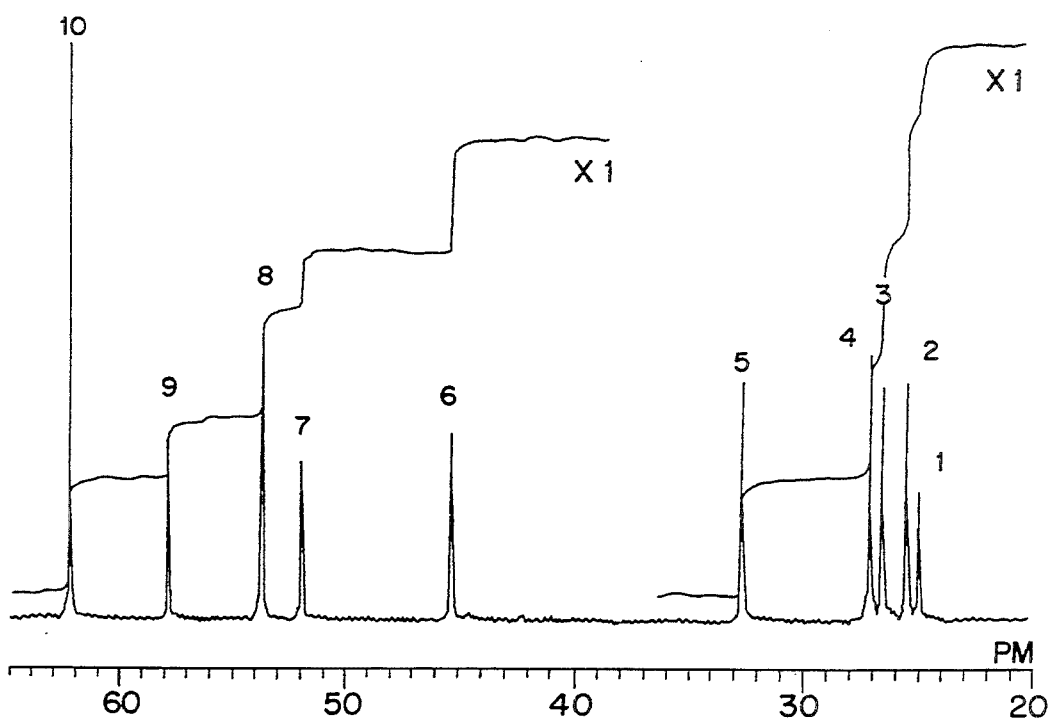
FIG. 1B

TERTIARY AMINOALCOHOL ANE PROCESS FOR PRODUCING THE SAME, AND, POLYURETHANE AND PROCESS FOR PRODUCING THE SAME

This application is a divisional of application Ser. No. 07/845,594, filed on Mar. 4, 1992, now U.S. Pat. No. 5,315,041 the entire contents of which are hereby incorporated by reference.

BACKGROUND OF THE INVENTION

1. Field of the Invention

The present invention relates to a novel tertiary aminoalcohol. The tertiary aminoalcohols per se are used as an emulsifier, epoxy hardener, urethane catalyst, flotation agent, extractant, additive for lubricating oil, and the like. Further derivatives of the tertiary aminoalcohols, such as quaternary ammonium salts, benzalkonium salts, carbobetaines and amine oxides can be used for various purposes. Particularly they can be converted into various derivatives, taking advantage of the characteristic structure thereof having a terminal alcohol, by modifying them through esterification, sulfation, phosphation, amination or halogenation.

The present invention relates to a novel polyurethane, a process for producing the same, and a process for producing a polyurethane foam. More particularly, the present invention is concerned with a process for producing a polyurethane which gives a polyurethane excellent moldability in mold filling substantially without the necessity for using a catalyst component commonly used for producing a polyurethane, a polyurethane produced by the process, a process for producing a rigid polyurethane foam excellent in mold filling, thermal insulation property and low-temperature dimensional stability, and a process comprising a spray step for producing a rigid polyurethane foam having excellent mechanical property and adhesive property whereby the reaction of a polyol with an Isocyanate can sufficiently proceed at low temperature. Furthermore, the present invention is concerned with a process for producing a foamed-in-mold flexible polyurethane foam for use in furniture and automobile cushions, more particularly, a process for producing a flexible polyurethane foam by using a urethane feedstock containing a particular tertiary aminoalcohol and having an excellent high temperature moldability at the time of pouring of a urethane feedstock in mold foaming.

2. Description of the Related Art

The inventors of the present invention do not know the fact that amino alcohols having a tert-amino group in the main chain thereof and a process for producing it like that of the present invention have been disclosed in known publications except for an ethylene oxide or propylene oxide adduct of an amine.

As for polyamines, a process for producing a polyamine having a terminal amino group by reacting a diol with $NH_3$ is disclosed in Japanese Patent Laid-Open Nos. 278528/1986 (Texaco) and 51646/1987 (W. R. Grace & Company), and a process for producing a polytertiary amine by the condensation reaction of a di-sec-amine with a diiodoaryl compound is disclosed in Japanese Patent Publication No. 29182/1989 (Xerox Corporation). Further a process wherein a polyalkylene polyamine is produced by the co-condensation of a lower diamine with hexamethylenediamine is disclosed in Japanese Patent Publication No. 311009/1987 (Nippon Oil Co., Ltd.), etc. As for the polyamine derivatives, a process wherein a polycation is produced by reacting a di-tert-amine with a dihalide is disclosed in Japanese Patent Publication Nos. 37242/1986 and 37243/1986 (L'Oreal).

However, tertiary aminoalcohols having a tert-amino group in the main chain skeleton thereof and a terminal hydroxyl group are utterly new compounds and no process has been known for the production thereof. If the production of such tertiary aminoalcohols is possible, the use thereof for a purpose different from that of ordinary amines and amine derivatives can be developed and, in addition, by the oligomerization or polymerization of the amines, characteristic properties different from those of the monomeric molecules of can be obtained. Thus the development of a new use of the amines is expected.

On the other hand, polyurethanes are used in various industrial fields, such as elastomer, rigid foam, semirigid foam, flexible foam and microcellular foam, by virtue of the ease of control of molding density, hardness of products and various properties, and their excellent moldability. In producing these polyurethanes, it is a common practice to use a tertiary amine or an organometallic catalyst as a polyurethane producing catalyst in addition to a polyisocyanate component and a polyol component for the purpose of promoting curing or foaming, which enables a polyurethane to be produced on an industrial scale.

Among the polyurethane producing catalysts, tertiary amines are widely used because they are useful for controlling the balance of the reaction. In many cases, however, they have a strong irritating odor and cause skin irritation and therefore cause problems of the working environment and have a drawback that the odor lowers the value, in particular the sales appeal of the product.

Further, when a rigid polyurethane foam or the like is molded by mold foaming for use in a refrigerator or a panel, an improvement in the mold filling relating to the fluidity of the resin within the mold is required, so that a method for lowering the density in a high yield has been desired in the art.

In recent years, the use of chlorofluorocarbons as a foaming agent has become legally regulated for the protection of the ozonosphere, and trichlorofluoromethane (R-11), which has hitherto been used for the production of a rigid polyurethane foam, is among the substances subject to regulation. This brings about a problem of the necessity for reducing the use of trichlorofluoromethane. Examples of the reduction means proposed in the art include increasing the amount of water used to reduce the amount of trichlorofluoromethane (the so-called "chlorofluorocarbons-poor formulation") and one wherein use is made of 1,1-dichloro-2,2,2-trifluoroethane (R-123), 2,2-dichloro-2-fluoroethane (R-141$b$), chlorodifluoromethane (R-22), 1,1,1-chlorodifluoroethane (R-142b) or 1,1,1,2-tetrafluoroethane (R-134$a$) having an ozone destruction factor (ODP) smaller than that of trichlorofluoromethane.

In the chlorofluorocarbons-poor formulation wherein the amount of water used as a foaming agent is increased, the increase in the amount of water inevitably accelerates the reaction of water with the polyisocyanate component. This causes the amount of formation of a urea bond derived from the evolution of carbon dioxide to be increased, so that the balance between the foaming reaction and the resinification reaction is lost, which causes the mold filling of the polyurethane foam to be significantly lowered. The use of 1,1-dichloro-2,2,2-trifluoroethane or 2,2-dichloro-2-fluoroethane instead of trichlorofluoromethane makes it necessary to increase the amount of use of water, because the low temperature dimensional stability, compressive strength and mold filling are lowered thereby. This, however, causes the mold filling to be further lowered.

The rigid polyurethane foam produced by a process comprising a spray step (a spray type rigid polyurethane foam, hereinafter) is used mainly for the thermal insulation of the internal wall and ceiling of houses and the thermal insulation of tanks. A special foaming machine is used for the foaming work of the spray type rigid polyurethane foam. An air spray foaming machine is a system wherein compressed air is introduced into a mixing gun, while an airless foaming machine is a system wherein a feedstock is introduced into a mixing gun through the use of a lightweight compressor and then sprayed. A liquid mixture comprising a polyol component and an isocyanate component is sprayed on a face of an article through the use of the above-described foaming machines, and a thermal insulation layer comprising a rigid polyurethane foam is formed on that face through the utilization of the properties of the mixture which allow rapid thickening, foaming and forming a high-molecular weight polymer.

The above-described useful spray type rigid polyurethane foam has found an expanded application, however, the increase in the amount of use thereof has brought about various problems. One of the problems is that the bonding strength between the foam and the adherend material is so poor, that the foam peels off or falls down with the lapse of time to impair the thermal insulation effect, so that dewing becomes liable to occur.

Further, the regulation of the use of chlorofluorocarbons such as trichlorofluoromethane has brought about a tendency that the amount of incorporation of water in the foaming agent is increased, which renders the above-described problems more serious. Specifically, when the amount of the chlorofluorocarbon subject to regulation is reduced by increasing the amount of incorporation of water, the agglomeration caused by a urea bond formed by the reaction of water with the Isocyanate violently occurs and further the boundary between the urethane foam and the adherend or the surface of the foam suffers from less accumulation of the heat of reaction, which brings about drawbacks such as a lack In the self-bonding strength which is the most important property of the spray type rigid polyurethane foam and an increase in the fragility. This tendency becomes conspicuous in conducting the spraying at a relatively low temperature of 5° C. or below.

The flexible hot mold foam is produced by blending and sufficiently mixing a polyether polyol, a polyisocyanate, a foaming agent, a silicone foam stabilizer and a catalyst with each other, pouring the mixture into a mold and then heating the mixture to allow a reaction to proceed. In this case, after the temperature of the mold is adjusted to 35° to 45° C., a urethane feed-stock is poured into the mold to conduct foaming and cured in a furnace at 160° to 200° C., and the cured foam is demolded. The reason why the temperature of the mold is adjusted to 35° to 45° C. resides in that when it is below 35° C., an increase in the foam density and insufficient curing of the foam are liable to occur, and further the time taken from the pouring to the demolding is lengthened, which hinders the production of the foam. When the temperature of the mold exceeds 45° C., a crack occurs within the foam, so that good products can not be obtained. Although trichlorofluoromethane is used in the production of a foam having a low density and a low hardness. It is desired to reduce or discontinue the use of trichlorofluoromethane for the reasons mentioned hereinabove.

Therefore, if a good foam can be uniformly produced at a mold temperature of 45° C. or above, the step of cooling the mold after the demolding of the foam in a foam production line can be remarkably omitted, which contributes to the prevention of energy loss. Further, the foam produced at a higher mold temperature has a lowered density due to an enhancement in the foaming efficiency. In attaining the same density as that of the foam at an ordinary mold temperature, the amount of the foaming agent can be reduced, whereby the use of the chlorofluorocarbons subject to regulation can be reduced or discontinued.

DISCLOSURE OF THE INVENTION

SUMMARY OF THE INVENTION

After intensive investigations made under these circumstances, the inventors have completed the present invention.

The present invention provides a tertiary aminoalcohol represented by the general formula (I):

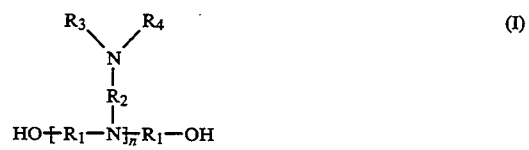

wherein $R_1$ each represents a straight-chain or branched alkylene group having 2 to 24 carbon atoms, a cycloalkylene group having 3 to 24 carbon atoms, a cycloalkyl alkylene group having 4 to 24 carbon atoms, an arylene group having 6 to 24 carbon atoms, an aralkylene group having 7 to 24 carbon atoms or $-(CH_2CH_2O)_p-(CH_2CH_2)_q-$ (p being 0 or a positive number and q being a positive number), $R_2$ each represents a straight-chain or branched alkylene group having 1 to 9 carbon atoms, $R_3$ each represents a straight-chain or branched alkyl group having 1 to 4 carbon atoms, $R_4$ each represents a straight-chain or branched alkyl group having 1 to 4 carbon atoms and n, which is an average polymerization degree, represents a positive number of 1 to 50.

The tertiary aminoalcohol, in which $R^1$ each represents a straight-chain or branched alkylene group having 3 to 9 carbon atoms, $R_2$ each represents a straight-chain or branched alkylene group having 1 to 3 carbon atoms, $R_3$ each represents a straight-chain or branched alkyl group having 1 to 4 carbon atoms, $R_4$ each represents a straight-chain or branched alkyl group having 1 to 4 carbon atoms and n represents a positive number of 2 to 10 in the general formula (I), is preferable.

The present invention also provides a tertiary aminoalcohol represented by the general formula (II):

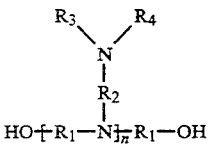

(II)

wherein $R_1$ represents a straight-chain or branched alkylene group having 2 to 24 carbon atoms, $-(CH_2CH_2O)_p-(CH_2CH_2)-$ (p being 0 or a positive number of 1 to 3), an alicyclic alkylene group or an aralkylene group, $R_2$ represents an alkylene group having 1 to 9 carbon atoms, $R_3$ and $R_4$ each represent an alkyl group having 1 to 4 carbon atoms, and n represents a positive number of 2 to 50.

The present invention provides a process for producing the above-described tertiary aminoalcohol represented by the general formula (I) by reacting a diol or dialdehyde with a diamine, wherein a catalyst comprising copper, a transition metal of the fourth period and a platinum group element of the group VIII, and optionally containing an alkali metal or an alkaline earth metal is used.

In the above-described process, the transition metal of the fourth period is preferably at least one selected from the group consisting of nickel and zinc, and the platinum group metal of the group VIII is preferably at least one selected from the group consisting of platinum, palladium, ruthenium and rhodium.

In the above-described process, the molar ratio of copper to the metal atom of the transition metal of the fourth period in the catalyst is preferably 1:9 to 9:1 and the molar ratio of the platinum group element of the group VIII to the total of copper and the transition metal of the fourth period in the catalyst is preferably 0.0001 to 0.1. The molar ratio of the platinum group metal of the group VIII to the total of copper and the transition metal of the fourth period in the catalyst is particularly preferably 0.001 to 0.1.

The present invention also provides a process for producing the above-described tertiary aminoalcohol represented by the general formula (II) by reacting a diol or dialdehyde with a diamine, wherein a catalyst comprising copper, a transition metal of the fourth period and a platinum group metal of the group VIII, and optionally containing an alkali metal or an alkaline earth metal is used.

Furthermore, the present invention provides a process for producing a polyurethane comprising a step of reacting a polyisocyanate component with a polyol component, wherein the above-described tertiary aminoalcohol represented by the general formula (I) is used as at least part of the polyol component.

The process for producing a polyurethane, in which $R_1$ each represents a straight-chain or branched alkylene group having 3 to 9 carbon atoms, $R_2$ each represents a straight-chain or branched alkylene group having 1 to 3 carbon atoms, $R_3$ each represents a straight-chain or branched alkyl group having 1 to 4 carbon atoms, $R_4$ each represents a straight-chain or branched alkyl group having 1 to 4 carbon atoms and n represents a positive number of 2 to 10 in the general formula (I), is preferable.

The present invention also provides a process for producing a polyurethane comprising a step of reacting a polyisocyanate component with a polyol component, wherein the above-described tertiary aminoalcohol represented by the general formula (III) is used as at least part of the polyol component:

(III)

wherein $R_1$ represents a straight-chain or branched alkylene group having 2 to 24 carbon atoms, an alicyclic alkylene group having 2 to 24 carbon atoms, an aralkylene group having 2 to 24 carbon atoms or a $-(CH_2CH_2O)_p-(CH_2CH_2)_q-$group (p being 0 or a positive number and q being a positive number);

$R_2$ represents a straight-chain or branched alkylene group having 1 to 9 carbon atoms;

$R_3$ and $R_4$ each represent a straight-chain or branched alkyl group having 1 to 4 carbon atoms;

and n is a positive number of 2 to 50.

The present invention provides a polyurethane produced by a process for produced comprising reacting a polyisocyanate component with a polyol component, wherein the above-described tertiary aminoalcohol represented by the general formula (I) is used as at least part of the polyol component.

Furthermore, the present invention provides a process for producing a polyurethane foam comprising reacting a polyisocyanate component with a polyol component in the presence of a foaming agent, wherein the above-described tertiary aminoalcohol represented by the general formula (I) is used as at least part of the polyol component.

In the process for producing a polyurethane foam, including 1 to 50% by weight of the tertiary aminoalcohol represented by the general formula (I) in the polyol component is preferable.

In the process for producing a polyurethane foam, preferably at least one compound selected from the group consisting of aliphatic amines and aromatic amines is used in the step of reacting a polyisocyanate component with the polyol component, and the more preferably the amount of the compound selected from the group consisting of aliphatic amines and aromatic amines is 1 to 30 parts by weight based on 100 parts by weight of the total amount of the polyol component.

In the process for producing a polyurethane foam, preferably at least one compound selected from the group consisting of triethanolamine, tolylenediamine and a diamine compound represents by general formula (v):

, $H_2N-R_5-NH_2$ . (V)

wherein $R_5$ represents a straight-chain or branched alkylene group having 2 to 8 carbon atoms, is used in the step of reacting a polyisocyanate component with the polyol component.

In the process for producing a polyurethane foam, preferably the foaming agent is at least one compound selected from the group consisting of $H_2O$, 1,1-dichloro-2,2,2-trifluoroethane, 2,2-dichloro-2-fluoroethane, chlorodifluoromethane, 1,1,1-chlorodifluoroethane and 1,1,1,2-tetrafluoroethane.

Furthermore, the present invention provides a process for producing a rigid polyurethane foam comprising a step of reacting a polyisocyanate component with a polyol component in the presence of a foaming agent, wherein the above-described tertiary aminoalcohol represented by the general formula (I) is used as at least part of the polyol component.

In the process for producing a rigid polyurethane foam, preferably the polyol component includes a polyol having the OH value being 1000 and above, and more preferably the polyol component includes ethyleneglycol and/or glycerol each having the OH value being 1000 and above.

In the process for producing a rigid polyurethane foam, preferably the average OH value of the polyol component is 800 and above.

The present invention provides a process for producing a flexible polyurethane foam comprising a step of reacting a polyisocyanate component with a polyol component in the presence of a foaming agent, wherein the above-described tertiary aminoalcohol represented by the general formula (I) is used as at least part of the polyol component.

In the process for producing a flexible polyurethane foam. Preferably the average OH value of the polyol component is 200 and below.

In the process for producing a flexible polyurethane foam, the case that the foaming agent is H$_2$O and the foaming agent is used in amount of 2 to 8 parts by weight based on 100 parts by weight of the total amount of the polyol component is preferable.

Furthermore, the present invention provides a process for producing a polyurethane foam by the spray method comprising spraying a mixture containing reacting raw materials and a foaming agent and reacting a polyisocyanate component with a polyol component in the presence of a foaming agent, wherein the above-described tertiary aminoalcohol represented by the general formula (I) is used as at least part of the polyol component, and H$_2$O is used as the foaming agent in amount of 2 to 8 parts by weight based on 100 parts by weight of the total amount of the polyol component.

In the process for producing a polyurethane foam by spray method, preferably the polyol component includes 1 to 50% by weight of the tertiary aminoalcohol represented by the general formula (I).

The process for producing a polyurethane foam by spray method is suitable for producing a rigid polyurethane foam.

The above-described tertiary aminoalcohols have the following features.

Since they have tertiary amino groups in their molecular skeleton, they exhibit a catalytic activity in the reaction of a polyisocyanate component with an active hydrogen compound. Further, the tertiary aminoalcohols, as such, react with an lsocyanate group by virtue of the presence of a terminal hydroxyl group and consequently are incorporated in the polyurethane resin skeleton. Further, since the tertiary aminoalcohols are a diol type, they neither inhibit an increase in the molecular weight of the polyurethane resin nor deteriorate the final properties. Therefore, unlike the conventional tertiary amine catalyst, the tertiary aminoalcohols per scare less liable to give out a bad odor, because they have a terminal hydroxyl group and the boiling points thereof are high. Therefore, though they are incorporated in the polyurethane resin skeleton, neither the polyurethane resin nor the polyurethane foam gives bad odor, so that no lowering of the commercial value of the product occurs.

The use of the above-described tertiary aminoalcohols as at least part of the polyol component in the production of a polyurethane and a polyurethane foam enables the production of a polyurethane and a polyurethane foam substantially without the necessity for using a catalyst such as a tertiary amine, and the resultant polyurethane and polyurethane foam have improved properties with respect of mold filling, thermal insulation, low-temperature dimensional stability, etc.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The diols to be used for producing the tertiary aminoalcohols of the present invention are straight-chain or branched having 2 to 24 carbon atoms, such as 1,3-propanediol, 1,4-butanediol, 1,5-pentanediol, 1,6-hexanediol, 1,9-nonanediol, 1,10-decanediol, 1,4-cyclohexanedimethanol and ethylene oxide adduct of bisphenol A, and may have an ether bond in the molecule, such as diethylene glycol, triethylene glycol, tetraethylene glycol. The dialdehydes to be used for producing the tertiary aminoalcohols of the present invention are those corresponding to the above-described diols.

The diamines usable for producing the tertiary aminoalcohols of the present invention include those of the following general formula (IV), such as N,N-dimethylpropylenediamine and N,N-dimethylethylenediamine:

wherein R$_2$ represents a straight-chain or branched alkylene group having 1 to 9 carbon atoms,
and R$_3$ and R$_4$ each represent a straight-chain or branched alkyl group having 1 to 4 carbon atoms.

The present invention provides new tertiary amino alcohol having a tert-amino groups in the main chain and hydroxyl groups at both ends obtained by reacting a diol or dialdehyde with a primary amino group of a diamine to introduce a tertiary amino group in the main chain, and a process for producing it.

The tertiary aminoalcohols of the present invention have structures represented by the above-described general formulae (I) to (III).

In the general formula (I), R$_1$ each represents a straight-chain or branched alkylene group having 2 to 24 carbon atoms, a cycloalkylene group having 3 to 24 carbon atoms, a cycloalkyl alkylene group having 4 to 24 carbon atoms, an arylene group having 6 to 24 carbon atoms, an aralkylene group having 7 to 24 carbon atoms or —(CH$_2$CH$_2$O)$_p$—(CH$_2$CH$_2$)$_q$— (p being 0 or a positive number, preferably being 0 to 15 and more preferably being 0 to 10. q being a positive number and preferably being 1 to 15), and preferably represents a straight-chain or branched alkylene group having 3 to 9 carbon atoms. When each $R_1$ is a cycloalkylene group or an arylene group, it may be substituted with a lower alkyl such as methyl and ethyl, and so on. When each $R_1$ is a cycloalkylalkylene group or an aralkylene group, it preferably has 1 to 6 carbon atoms in the alkylene group is. The term "aralkylene group" as used herein is intended to mean a divalent group formed by removing one hydrogen atom from the aromatic ring of an aralkyl group, that is, an alkyl group having an aromatic ring, such as a benzyl group or a phenethyl group.

In the general formula (I), $R_2$ each represents a straight-chain or branched alkylene group having 1 to 9 carbon atoms, and preferably represents a straight-chain or branched alkylene group having i to 4 carbon atoms. In the general formula (I), $R_3$ each represents a straight-chain or branched alkyl group having 1 to 4 carbon atoms, and $R_4$ each represents a straight-chain or branched alkyl group having 1 to 4 carbon atoms. In the general formula (I), n, which is an average polymerization degree, represents a positive number of 1 to 50, preferably represents a positive number of 2 to 10.

When the number of carbon atoms in $R_1$ exceeds 9 and n is larger than 10, the resultant tertiary aminoalcohol(s) has an increased molecular weight and an increased viscosity depending upon the number of carbon atoms and structure of $R_2$. As a result, the obtained tertiary aminoalcohol tends to be unusable. On the other hand, when the number of carbon atoms of the $R_1$ is smaller than 2 and n is smaller than 2, the content of the tertiary amino group in the molecular skeleton becomes so low that no expected catalytic property can be obtained.

The tertiary aminoalcohol represented by the general formula (I) includes those where $R_1$ each represents a straight-chain or branched alkylene group having 3 to 9 carbon atoms. $R_2$ each represents a straight-chain or branched alkylene group having 1 to 3 carbon atoms, $R_3$ each represents a straight-chain or branched alkyl group having 1 to 4 carbon atoms, $R_4$ each represents a straight-chain or branched alkyl group having 1 to 4 carbon atoms and n represents a positive number of 2 to 10.

In the general formula (II), $R_1$ represents a straight-chain or branched alkylene group having 2 to 24 carbon atoms, $—(CH_2CH_2O)_p—(CH_2CH_2)—$ (p being 0 or a positive number of 1 to 3), an alicyclic alkylene group or an aralkylene group, $R_2$ represents an alkylene group having 1 to 9 carbon atoms, $R_3$ and $R_4$ each represent an alkyl group having 1 to 4 carbon atoms, and n represents a positive number of 2 to 50.

In the general formula (III), $R_1$ represents a straight-chain or branched alkylene group having 2 to 24 carbon atoms, an alicyclic alkylene group having 2 to 24 carbon atoms, an aralkylene group having 2 to 24 carbon atoms or a $—(CH_2CH_2O)_p—(CH_2CH_2)_q—$ group (p being 0 or a positive number and q being a positive number); $R_2$ represents a straight-chain or branched alkylene group having 1 to 9 carbon atoms; $R_3$ and $R_4$ each represent a straight-chain or branched alkyl group having 1 to 4 carbon atoms; and n is a positive number of 2 to 50.

Thus, the selection of the content of the tertiary amino group in the molecular skeleton, molecular weight, and the molecular weight and structure of the side chain in such a range as to satisfy the performance requirement of the polyol gives tertiary aminoalcohol having various catalytic properties in conformity with the required reactivity, so that it becomes possible to produce various polyurethanes substantially without the necessity for using any catalyst component.

Next, the process for producing a tertiary aminoalcohol of the present invention will be described.

Although techniques of the tertiary amination of a primary amino group are disclosed in Japanese Patent Publication Nos. 549/1982 and 12106/1984, Japanese Patent Laid-Open No. 55704/1982, Japanese Patent Publication Nos. 1297/1985 (Hoechst) and 48499/1985 (Shell), U.S. Pat. Nos. 4,404,403, 4,404,404 and 4,409,339 (Onyx), Japanese Patent Laid-Open Nos. 60636/1986 (Shering) and 14457/1984 (Texaco) and Japanese Patent Publication No. 28947/1987 (New Japan Chemical Co., Ltd.), these processes are insufficient, since the catalysts described therein have no sufficient reactivity and cannot provide the intended product in a sufficiently high yield.

On the contrary, the catalyst used in the present invention comprises copper, a transition metal of the fourth period and a platinum group metal of group VIII, and may optionally contain an alkali metal or an alkaline earth metal, and for the first time when this catalyst is used in the process for producing a tertiary amino alcohol, the intended tertiary amino alcohol can be provided in a sufficiently high yield.

The transition metal element of the fourth period constituting the catalyst which comprises copper, a transition metal of the fourth period and a platinum group metal of the group VIII is preferably at least one selected from the group consisting of nickel and zinc, and the platinum group metal of the group VIII is preferably at least one selected from the group consisting of platinum, palladium, ruthenium and rhodium. The molar ratio of copper to the metal atom of the transition metal of the fourth period in the catalyst is preferably 1:9 to 9:1. The molar ratio of the platinum group metal of the group VIII to the total of copper and the transition metal of the fourth period is preferably 0.0001 to 0.1, particularly preferably 0.001 to 0.1.

Although the catalyst to be used in the present invention essentially comprises copper, the transition metal of the fourth period and the platinum group metal as metal components, it may further contain an alkali metal or an alkaline earth metal.

The catalyst suited for use in the present invention can be used in various forms. Namely, the effect according to the interaction of the three components, i.e. copper, the transition metal of the fourth period and the platinum group metal of the group VIII, or the four components including them and the alkali metal or the alkaline earth metal (hereinafter referred to as "the fourth component") can be obtained for the first time when all of them are present in the reaction system as components of the catalyst.

In the catalyst used in the present invention, the above-described three of four components exhibit an essential catalytic function. Namely, the catalyst exhibits the catalytic activity in the reaction of the diol or dialdehyde with the amine for the first time when the respective metal components are reduced in a hydrogen atmosphere. Therefore, the forms of the metals prior to the reduction or the difference in the state of the reaction system after the reduction is not particularly limited in the present invention. The forms of the catalyst are not limited as far as the interaction between copper, the transition metal of the fourth period, the platinum group metal of the group VIII and, if necessary, the fourth component is exhibited after the reduction in a hydrogen atmosphere.

Therefore, the forms of the metals suitable for use as the catalyst in the production process of the present invention include:
1) those dispersible in the reaction medium, such as copper, the transition metal of the fourth group, the platinum group metal of the group VIII and, if necessary, the metal as the fourth component, oxides thereof, hydroxides thereof, and mixture thereof,
2) those dispersible in the reaction medium, such as a mixture of copper, the transition metal of the fourth group, the platinum group metal of the group VIII and the fourth component each carried by a suitable support, and the three components, i.e. copper, the transition metal of the fourth group and the platinum group metal of the group VIII, or the four components, i.e. these three components and the fourth component, carried together by a suitable support,
3) those capable of forming a metallic colloid in the reaction medium to form a homogeneous system, such as aliphatic carboxylic acid salts of the three components, i.e. copper, the transition metal of the fourth period and the platinum group metal of the group VIII, or the four components, i.e. these three components and the fourth component, and a complex of them stabilized with a suitable ligand, and
4) a mixture of those dispersible in the reaction medium as in the items 1) or 2) with those capable of forming a homogeneous system in the reaction medium as in the item 3), or those which are in the dispersion form prior to the reduction with hydrogen and in the homogeneous form after the reduction.

It will suffice when the interaction of the metals of the three or four components which are indispensable components of the catalyst used in the present invention is exhibited by the treatment in a hydrogen atmosphere.

From the viewpoint of the stabilization of the catalytic metals, namely, the fixation of the active surface and the resistance to a catalyst poison, a still preferred form of the catalyst used in the present invention is one obtained by homogeneously supporting the above-described metal components on a suitable support.

When the three metal components, i.e. copper, the transition metal of the fourth period and the platinum group metal of the group VIII, or the four components, i.e. these three components and the fourth component are to be supported, supports usable herein are those ordinarily used as a catalyst support, such as alumina, silica/alumina, diatomaceous earth, silica, active carbon, and natural and artificial zeolites. The amount of the catalytic metals to be supported by the support is not particularly limited. It is usually preferably 5 to 70% by weight based on the weight of the support.

The method for supporting the three or four metal components on the support surface can also be selected from various methods. The form of the starting catalytic metals may be oxides, hydroxides or salts of copper, the transition metal of the fourth period, the platinum group element of the group VIII and the fourth component. The metal salts include chlorides, sulfates, nitrates, acetates and aliphatic carboxylic acid salts of copper, the transition metal of the fourth period, the platinum group metal of the group VIII, and the fourth component. Further complexes of these metals, such as acetylacetone complexes and dimethylglyoxime complexes of copper, the transition metal element of the fourth period, the platinum group metal of the group VIII and the fourth component are also usable. In addition, a carbonyl complex, amine complex or phosphine complex of the platinum group metal of the group VIII can also be used.

In order to produce the catalyst by supporting the metals on the support by using these starting metal materials, any known methods can be employed. They include a method comprising putting the support in a solution containing suitable salts of copper, the transition metal of the fourth period, the platinum group metal of the group VIII and the fourth component to sufficiently impregnate the support with them and drying and firing the support (impregnation method); a method comprising mixing the support thoroughly with an aqueous solution of suitable salts of copper, the transition metal of the fourth period and the platinum group metal of the group VIII, and adding an aqueous alkali solution such as sodium carbonate aq. soln., sodium hydroxide aq. soln. and aqueous ammonia to precipitate the metal salts on the support, or, alternatively, adding an aqueous solution of suitable salts of copper, the transition metal of the fourth period and the platinum group metal of the group VIII and an aqueous alkali solution such as sodium carbonate aq. soln., sodium hydroxide aq. soln. and aqueous ammonia simultaneously to an aqueous slurry of the support in such a manner that a slurry having a stabilized pH value of, e.g., 7 will be obtained to precipitate the metal salts on the support, drying and firing them to prepare a catalyst comprising copper, the transition metal of the fourth period and the platinum group metal of the group VIII, and, when a catalyst comprising the four components are to be produced, putting the resultant catalyst comprising the three components in an aqueous solution of an alkali metal salt or an alkaline earth metal salt to thoroughly impregnate it, and drying and firing it to obtain the catalyst comprising the four components (a combination of co-precipitation method and impregnation method); and a method comprising conducting ion exchange with hydrogen or a metal contained in zeolite (ion exchange method). In the co-precipitation method, the catalyst is thoroughly washed with water after the deposition of the metals and is dried around 100° C. and fired at 300° to 700° C. to obtain the intended catalyst.

Another method is also effective wherein only copper or only copper and the transition metal of the fourth period are carried on the support and, prior to the reaction, the platinum group metal of the group VIII and, if necessary, the fourth component carried on a support or its (their) aliphatic carboxylic acid salt or its (their) complex is added thereto to form a composite of copper, the transition metal of the fourth period, the platinum group metal of the group VIII and, if-necessary, the fourth component in a reaction medium in a hydrogen atmosphere.

The catalyst prepared by any of the above-described methods is preferably in such a form that the three or four components are homogeneously supported on one support.

The three components, i.e. copper, the transition metal of the fourth period and the platinum group metal of the group VIII, are essentially indispensable in the catalyst used in the present invention.

A detailed description will be made of the process for producing the tertiary aminoalcohol of the present invention.

In the production of a tertiary aminoalcohol by continuously reacting a diol or dialdehyde with a diamine, the object of the present invention can be attained by conducting the reaction In the presence of a reduced catalyst comprising copper, a transition metal of the fourth period such as nickel, chromium, zinc, manganese, iron and cobalt, and a platinum group metal of the group VIII, or the same reduced catalyst as this which further contains an alkali metal or an alkaline earth metal at 150° to 250° C. under atmospheric or elevated pressure while water formed by the reaction is continuously or intermittently removed from the reaction system. The diol or dialdehyde may be continuously added in the course of the reaction or added at once in the initial stage or a predetermined amount thereof may be added in portions. The diamine may be added continuously or intermittently in the course of the reaction or a predetermined amount thereof may be added at once.

The molar ratio of the diamine to the diol or dialdehyde should be 0.7 or more, preferably 1 or more.

In the production process of the present invention, water formed by the reaction of the diol or dialdehyde with the diamine is preferably removed from the reaction system. When the water is not removed, the catalytic activity and selectivity are often deteriorated. For example, when the reaction is conducted without removing the formed water, disproportionation products of the amine or aldehyde condensates are formed in a large amount to reduce the yield of the intended tertiary aminoalcohol.

Water thus formed can be removed either continuously or intermittently in the course of the reaction so far as the water is not kept in the reaction system for a long time but properly removed. It is desirable, however, to continuously remove the formed water each time. In particular, it is a usual practice to blow a suitable amount of hydrogen gas into the reaction system in the course of the reaction to expel the formed water together with the hydrogen gas. Hydrogen gas can be recirculated by separating the formed water by condensation in a condenser. Further a suitable solvent is added to the reaction system to distill the formed water by azeotropically with the solvent or, alternatively, an inert solvent may be used for the purpose of depressing the viscosity of the reaction mixture.

In the present invention, the catalyst may be previously reduced with hydrogen gas or it may be reduced by putting it in the reactor together with the starting diol or dialdehyde and reducing it by heating to the reaction temperature while hydrogen gas is blown thereinto.

An embodiment of the process for producing the tertiary aminoalcohol of the present invention will be simply described below.

The starting diol or dialdehyde and the catalyst are fed into a reactor provided with a hydrogen inlet tube, condenser and separator for condensing and thereby separating water formed by-the reaction, excessive amine and an oily substance evaporated. Although the amount of the catalyst is not particularly limited, it usually ranges from 1 to 10% by weight based on the diol or dialdehyde.

After purging air in the reaction system with nitrogen gas, heating is started while hydrogen is blown in. The diamine is added at once or slowly in portions to the reaction system after the temperature reaches a predetermined point. The reaction temperature is usually about 150° to 250° C., but a temperature beyond this range can be employed depending on the starting materials used. The catalyst is activated by reduction during the temperature elevation. After reaching the predetermined temperature, the diamine is introduced thereinto or dropwise added thereto to start the reaction.

Water formed by the reaction is discharged from the reaction system together with hydrogen and passed through the condenser and separator to separate it from oily substances. The separated oily substances are returned to the reactor. After the completion of the reaction, the catalyst is filtered off by a suitable method to obtain the intended product.

The polyisocyanate component to be used in the processes for producing a polyurethane according to the present invention may be an aromatic, aliphatic or alicyclic polyisocyanate having at least two isocyanate groups, a mixture of two or more of such polyisocyanates or a modified polyisocyanate derived therefrom. Examples thereof include polyisocyanates such as tolylene diisocyanate, diphenylmethane diisocyanate, polymethylene polyphenyl polyisocyanate, Crude MDI, xylylene diisocyanate, isophorone diisocyanate and hexamethylene diisocyanate; modified polyisocyanates derived therefrom, such as carbodiimides and biurets derived therefrom and dimers and trimers thereof; and isocyanate-terminated prepolymers prepared from these polyisocyanates and compounds having active hydrogens.

According to the present invention, the tertiary aminoalcohol represented by the general formula (I) can be used at an arbitrary ratio as the polyol component to thereby control the catalytic performance. Further, the tertiary aminoalcohol represented by the general formula (III) can be used at an arbitrary ratio as the polyol component to thereby control the catalytic performance.

In the present invention, a polyurethane having a desirable form and necessary physical properties can be obtained by using the above-described tertiary aminoalcohol together with other polyols. The polyol to be used together with the tertiary aminoalcohol may be the conventional polyester polyol or polyether polyol. Examples thereof include polyester polyols prepared from the conventional dibasic acid and the conventional polyhydric alcohol; and polyether polyols prepared by the addition reaction of a polyhydric alcohol such as glycol, glycerol, pentaerythritol, trimethylolpropane and sucrose or a polyamine such as triethylenediamine, 1,3-propanediamine and isophoronediamine with ethylene oxide and/or propylene oxide, which may be used alone or as a mixture of two or more of them.

According to the present invention, if necessary, various additives such as catalyst, surfactant, foam stabilizer, colorant, flame retardant and/or stabilizer may be used in addition to the polyisocyanate component and polyol component described above. These additives may be each selected from among the conventional ones and the amounts thereof may be selected each in the conventional range.

Although the use of a catalytic component is substantially unnecessary when the tertiary aminoalcohol according to the present invention is used as at least part of the polyol component, the conventional catalyst may be used in the production of the polyurethane for some uses in order to improve the moldability and processability during the production of the polyurethane.

Although such a catalyst is not particularly limited, the catalyst includes known amine catalysts, for example, N,N,N,N-tetramethylhexamethylenediamine, N,N,N,N-tetramethylpropylenediamine, N,N,N,N,N-pentamethyldiethylenetriamine, N,N,N,N-tetramethylethylenediamine, N-methyl-N'-dimethylaminoethylpiperazine, N,N-dimethylaminocyclohexylamine, bis(dimethylaminoethyl)ether, tris(N,N-dimethylaminopropyl)hexahydro-S-triazine, methylmorpholine, ethylmorpholine, triethylenediamine, 1-methylimidazole, 1,2-dimethylimidazole and 1-isobuthyl-2-methylimidazole, and known metal catalysts, for example, tin octanoate, tin dibutydilaurate and lead octanoate. These catalysts may be used either alone or as a mixture of two or more of them together with the tertiary aminoalcohol.

In the present invention, a crosslinking agent may be used at need. Such a crosslinking agent includes glycols such as ethylene glycol, propylene glycol, diethylene glycol and 1,4-butanediol; polyhydric alcohols such as glycerol, pentaerythritol and sorbitan; alkanolamines such as diethanolamine and triethanolamine; aliphatic polyamines such as ethylenediamine and diethylenetriamine; and aromatic diamines such as 4,4-diphenylmethanediamine.

The process for producing a polyurethane according to the present invention can be summed up as follows:

A mixture A containing the above-mentioned polyol component as a main component is reacted with a mixture B containing the above-mentioned polyisocyanate component as a main component. Components other than the polyol component and polyisocyanate component are incorporated into the mixture A or B. The reaction conditions are not particularly limited.

The present invention also provides a polyurethane producing by the above-described process.

The process for producing a polyurethane foam according to the present invention is conducted by using a polyisocyanate component, a polyol component and a foaming agent, and at least one tertiary amino alcohol represented by the above general formula (I) is used as at least part of the polyol component.

In the process for producing a polyurethane foam according to the present invention, a tertiary aminoalcohol represented by the above general formula (I) is preferably used in an amount of 1 to 50% by weight, more preferably used in amount of 1 to 30% by weight based on the polyol component.

It is preferable to use at least one compound selected from the group consisting of water (H₂O), 1,1-dichloro-2,2,2-trifluoroethane, 2,2-dichloro-2fluoroethane, chlorodifluoromethane, 1,1,1-chlorodifluoroethane and 1,1,1,2-tetrafluoroethane as the foaming agent. If necessary, methylene chloride, pentane or n-hexane may be used in order to reduce the amount of the trichlorofluoromethane to be used.

Further, in the process for producing a polyurethane foam according to the present invention, it is preferable to use at least one compound selected from the group consisting of aliphatic amines and aromatic amines in addition to the above components. The amount of the aliphatic or aromatic amine to be additionally used is preferably 1 to 30 parts by weight based on 100 parts by weight of the total amount of the polyol component. Preferable examples of the aliphatic and aromatic amines include triethanolamine, tolylenediamine and diamines represented by the following general formula (V):

$$H_2N-R_5-NH_2 \qquad (V)$$

wherein $R_5$ represents a straight-chain or branched alkylene group having 2 to 8 carbon atoms.

In the process for producing a polyurethane foam according to the present invention, the polyisocyanate components and the polyol components described above with respect to the process for producing a polyurethane according to the present invention are all usable, and other arbitrary components may be also used, so far as they are those conventionally used for producing a polyurethane foam.

The present invention also provides a process for producing a rigid or flexible polyurethane foam and a process for producing a polyurethane foam by spray method, which will now be described respectively.

[I] Process for producing rigid polyurethane foam

In producing a rigid polyurethane foam, it is preferable to use a polyol having a hydroxyl (OH) value of 1000 or above simultaneously as part of the polyol component and examples thereof include ethylene glycol and glycerol, which have a hydroxyl value of 1000 or above. Further, it is desirable that the average hydroxyl value of the polyol component to be used in the production of a rigid polyurethane foam is 300 or above.

In the production of a rigid polyurethane foam, the balance between the rate of gas evolution and the curing rate of the resin is an important factor for improving the mold filling property. When the rate of gas evolution is higher than the curing rate of the resin, the incorporation of the gas in the resin is so insufficient as to fail to give a necessary foam volume, thus resulting in a poor mold filling, while when the curing rate of the resin is higher than the rate of gas evolution, the resin will be too viscous to exhibit sufficient flowability, resulting in a poor mold filling.

Even when using water and trichlorofluoromethane at an ordinary ratio as a foaming agent in the production of a rigid polyurethane foam, the balance desirable for the mold filling between the rate of gas evolution and the curing rate of the resin is upset if the amount of the polyol or catalyst is changed to enhance the curing rate of the resin to thereby improve the productivity, so that the resulting rigid polyurethane foam exhibits poor mold filling. According to the present invention, the tertiary aminoalcohol represented by the general formula (I) used as part or the whole of the polyol component accelerates not only the resinification in the initial stage of the reaction but also the gasification of trichlorofluoromethane, by which the balance desirable for mold filling between the rate of gas evolution and the curing rate of the resin maintained to give excellent mold filling.

In a fluorocarbons-poor formulation containing a reduced amount of trichlorofluoromethane, an increased amount of water is used, so that rapid foaming and curing to give a rigid polyurethane foam poor in mold filling. When the tertiary aminoalcohol represented by the general formula (I) is used in such a fluorocarbons-poor formulation, no conventional catalytic component is necessary and the reaction of an isocyanate group with water is depressed by virtue of the nature of the tertiary aminoalcohol (I), so that the mold filling of the foam is not impaired.

Further, when 1,1-dichloro-2,2,2-trifluoroethane or 2,2-dichloro-2-fluoroethane is used instead of trichlorofluoroethane, the mold filling of the resulting rigid polyurethane foam is lowered due to a lowering in the resinification rate and the accompanying delay of the evolution in chlorofluorocarbon gas caused by the difference in boiling point and solubility in the resin between these fluorocarbons and trichlorofluoromethane, which is thought to be the defect of these fluorocarbons. According to the present invention, however, the resinification of such a formulation can be accelerated by the use of the tertiary aminoalcohol represented by the general formula (I) to give a rigid polyurethane foam having excellent mold filling property.

The polyisocyanate component, polyol component and foaming agent to be used in the process for producing a rigid polyurethane foam according to the present invention may be each any one selected from among those described above and also other arbitrary components may be used, so far as they are those conventionally used in the production of a rigid polyurethane foam.

Further, the reaction conditions to be employed in the production are not particularly limited.

[II] Process for producing flexible polyurethane foam

With respect to the production of a flexible polyurethane foam, the inventors of the present invention have found that the production of a crack-free excellent foam at a high mold temperature becomes possible by using a tertiary aminoalcohol represented by the general formula (I) and a specified amount of water as a foaming agent.

The polyisocyanate component and polyol component other than the tertiary aminoalcohol to be used in the process for producing a flexible polyurethane foam according to the present invention may be each any one conventionally used in the production of a flexible polyurethane foam. In producing a flexible polyurethane foam according to the present invention, it is preferable that the polyol component used has an average hydroxyl value of 200 or below. Further, it is preferable to use water as a foaming agent in an amount of 2 to 8 parts by weight based on 100 parts by weight of the total of the polyol component. Of course, a fluorocarbon foaming agent may be suitably used together with water. Other arbitrary components may be also used, so far as they are those conventionally used in the production of a flexible polyurethane foam. Although the reaction conditions to be employed in the production of a flexible polyurethane foam according to the present invention are not particularly limited, the reaction can be conducted at a mold temperature higher than that of the prior art.

Further, the above description of the process for producing a polyurethane foam according to the present invention can be also summed up as follows:

A mixture A containing the above-mentioned polyol component as a main component is reacted with a mixture B containing the above-mentioned polyisocyanate component as a main component. A foaming agent is preferably incorporated into the mixture A, though it may be incorporated into either the mixture A or the mixture B. Components other than the polyol component and polyisocyanate component are incorporated into the mixture A or B. The reaction conditions are not particularly limited.

[III] Process for producing rigid polyurethane foam by spray method

The process for producing a rigid polyurethane foam by the spray method according to the present invention comprises steps of spraying a mixture comprising a polyisocyanate component, a polyol component and a foaming agent and reacting the polyisocyanate component with the polyol component in the presence of the foaming agent, wherein at least one tertiary aminoalcohol represented by the above general formula (I) is used as at least part of the polyol component, and water is used as the foaming agent in an amount of 2 to 8 parts by weight based on 100 parts by weight of the total amount of the polyol component.

In this process, the amount of the tertiary aminoalcohol represented by the above general formula (I) is preferably 1 to 50% by weight based on the total amount of the polyol component.

In producing a rigid polyurethane foam by the spray method, the rate of the reaction of a polyol component containing a tertiary aminoalcohol represented by the general formula (I) with an Isocyanate component can be enhanced in proportion to the amount of the tertiary aminoalcohol added, and further the reaction can be advanced even at a temperature as low as 5° C. or below. As described above, when the above starting material mixture for producing a rigid polyurethane foam is applied to an adherend by spraying, the reaction of the mixture proceeds sufficiently even at low temperature, so that the insulating layer (a rigid polyurethane foam) thus formed exhibits necessary mechanical properties and adhesive strength and therefore does not peel or come off from the surface of the adherend.

Further, even when using a foaming agent system comprising a reduced amount of a fluorocarbon, the use of which is regulated, for example, trichlorofluoromethane, and an increased amount of water, the resulting foam exhibits a desirable adhesive strength, so that it does not peel or come off even though the spraying of the above starting material mixture and reaction between the starting materials were conducted at a temperature as low as 5° C. or below.

The polyisocyanate component and polyol component to be used in the process for producing a rigid polyurethane foam by the spray method according to the present invention may be each any one selected from among those described above with respect to the process for producing a polyurethane according to the present invention and, if necessary, a foaming agent other than water may be used simultaneously. Further, other arbitrary components may be used, so far as they are suitable for the production of a rigid polyurethane foam by the spray method. The production of a rigid polyurethane foam by the spray method according to the present invention can be conducted at a temperature lower than that of the prior art, though the reaction conditions to be employed therein are not particularly limited.

Furthermore, the above description on the process for producing a rigid polyurethane foam by the spray method according to the present invention can be summed up as follows:

A mixture A containing the above mentioned polyol component as a main component and a mixture B containing the above-mentioned polyisocyanate component as a main component are mixed with each other. The obtained mixture is sprayed onto the surface of the adherend and raw materials having reactivity in the mixture are reacted. A foaming agent is preferably incorporated into the mixture A, though it may be incorporated into either the mixture A or the mixture B. Components other than the polyol component and polyisocyanate component are incorporated into the mixture A or B. The reaction conditions are not particularly limited.

As illustrated above, the use of the tertiary aminoalcohol according to the present invention enables the production of a polyurethane or a polyurethane foam in the substantial absence of an additional catalyst, by which not only the working atmosphere in the production of a polyurethane or a polyurethane foam but also the performance of the product can be remarkably improved.

Particularly in the production of a polyurethane foam, the following effects can be attained:

① polyurethane foam satisfactory in both density and mold filling property can be obtained even when use is made of a foaming agent system comprising an increased amount of water and a reduced amount of a fluorocarbon, ② particularly, a rigid polyurethane foam satisfactory in both density and mold filling property can be obtained even when use is made of a fluorocarbon foaming agent other than R-11, ③ when a rigid polyurethane foam is produced by spray method, the obtained rigid polyurethane foam is excellent in properties such as self adhesive bonding strength at low temperature, and ④ the production of a flexible polyurethane foam can be conducted at a mold temperature higher than that of the prior art to thereby simplify the production process. Further, even when the production is conducted at the conventional temperature, the amount of the foaming agent to be used can be reduced.

BRIEF DESCRIPTION OF THE DRAWINGS

FIG. 1 shows the mass spectrum of the tertiary amino alcohol obtained in Example A.

EXAMPLES

Figure 2:
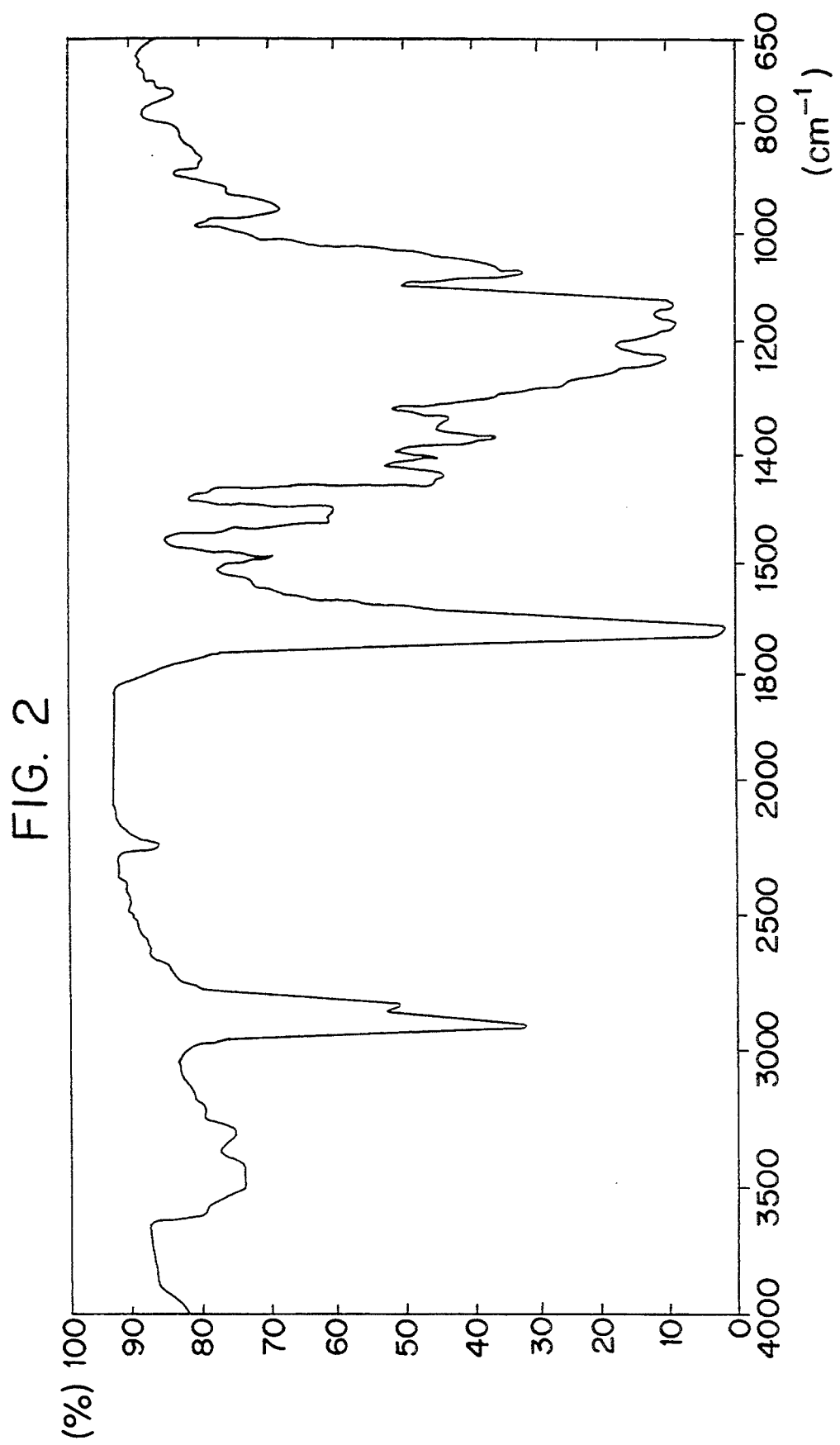
FIG. 2 shows the infrared spectrum of the polyurethane obtained in Example 1.

The present invention will now be described by referring to the following examples, though the present invention is not limited by them.

<Preparation of the catalyst>

Three components catalysts in which copper, a transition metal of the fourth period and a platinum group metal of the group VIII were supported on a synthetic zeolite, were prepared as follows:

(Catalyst A)

A synthetic zeolite was placed in a 1-l flask. Then copper nitrate, nickel nitrate and ruthenium chloride were dissolved in water in such amounts that the molar ratio of the metal atoms would be Cu:Ni:Ru of 4:1:0.01 and the obtained solution was fed into the 1-l flask. The obtained mixture was heated with stirring. A 10% aqueous $Na_2CO_3$ solution was slowly dropwise added thereto at 90° C. After completion of this addition, the obtained mixture was aged for 1 hour. Then, the obtained precipitates were separated by filtration, washed with water, dried at 80° C. for 10 hours, and then fired at 600° C. for 3 hours. The amount of the metal oxides thus carriered was 50% by weight based on the weight of the support, namely the synthetic zeolite.

(Catalyst B)

A catalyst having a molar ratio of Cu:Zn:Pd of 5:1:0.1 was prepared in the same manner as that described above.

Four components catalysts which copper, a transition metal of the fourth period, a platinum group metal of the group VIII and an alkali metal were supported on a synthetic zeolite were prepared as follows:

(Catalyst C)

A catalyst having a molar ratio of Cu:Ni:Ru of 4:1:0.01 was prepared in the same manner as that described above, and then the catalyst comprising the three components thus obtained was thoroughly immersed in an aqueous lithium carbonate solution (with a molar ratio of Ni:Li of 1:0.05). Then, the catalyst was separated by filtration, washed with water, dried again at 80° C. for 10 hours, and fired at 300° C. for 1 hour to obtain a catalyst comprising the four components, i.e. Cu/Ni/Ru/Li.

The catalysts thus prepared were used in the following examples.

(Example A) Synthesis of a tertiary aminoalcohol 1,6-Hexanediol was reacted with N,N-dimethylpropylenediamine.

600 g of 1,6-hexanediol and 12 g (2% by weight based on the starting alcohol) of the above-described catalyst A were fed in a 2-l flask provided with a condenser and separator for separating the formed water. Air in the vessel (flask) was purged with nitrogen and heating was started. When the temperature in the reaction system had reached 100° C., hydrogen gas was blown into the reaction system at a rate of 40 l/h with a flowmeter and the temperature was elevated to 200° C. 1000 g of N,N-dimethylpropylenediamine was added at once to the reaction system at that temperature. The progress of the reaction was traced by means of the amine value and hydroxyl value. The reaction was conducted for about 5 hours. After the completion of the reaction, the catalyst was separated by filtration. A pale brown, viscous liquid was obtained as a product.

Then the product was analyzed.

According to the mass analysis, it was found from the molecular weight that the tertiary amino alcohols of the following formula wherein n represents 2 to 4 were formed:

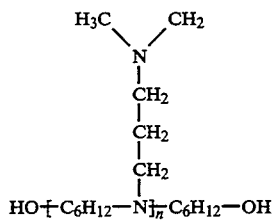

To prove that it is terminated by hydroxyl groups, the $^{13}$C-NMR spectrum of the product was determined with 270 MHz NMR (JNM-GX270WB). The spectrum is given in FIG. 1. From the area ratio, it was found that 94% of the terminal groups comprised hydroxyl groups.

According to VPO determination, the average molecular weight was 613 and the average n was 2.7. The average value of n calculated from the $^{13}$C spectrum was 2.3, which coincided with the found value. As for the amine values, the total amine value found (512) was very close to the calculated one (502 when n was 3) and the tertiary amine value found (512) was very close to the calculated one (502 when n was 3). It was thus confirmed that the tertiary amino alcohol of this structure had been obtained.

(Example B) Synthesis of a tertiary aminoalcohol

The reaction was conducted for about 8 hours under the same conditions as those of the Example B except that the reaction temperature was altered to 190° C., 1,9-nonanediol was used as the diol, 2% by weight, based on the starting alcohol, of the catalyst B was used as the catalyst, and N,N-dimethylethylenediamine was used as the diamine.

The product was the compound of the following formula having an average molecular weight of 892 (VPO), n of 3–12 (Mass) and terminal OH content of 93% (NMR).

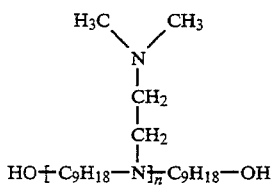

(Example C) Synthesis of a tertiary aminoalcohol

The reaction was conducted for 15 hours in the same manner as that of the Example A except that the reaction temperature was altered to 220° C., triethylene glycol was used as the alcohol, catalyst C (4% by weight based on the starting alcohol) was used as the catalyst, and N,N-dibutylpropylenediamine was used as the diamine.

The product had an average molecular weight of 813 (VPO), n of 2–4 (Mass) and terminal OH content of 84% (NMR).

(Example D) Synthesis of a tertiary aminoalcohol 600 g of 1,6-hexanediol and 12 g (2% by weight based on the starting alcohol) of a Cu/Ni/Pd catalyst were fed into a 2-l flask fitted with a condenser and a separator for removing the water formed. The system was purged with nitrogen while stirring the contents and the heating of the system was started. After the bulk temperature had reached 100° C., hydrogen gas was blown into the system at a flow rate of 40 l/hr with a flowmeter and the temperature of the system was raised to 200° C. 1000 g of N,N-dimethylpropylenediamine was added to the reaction system at once at this temperature. The reaction was monitored based on the amine value and the hydroxyl value. The reaction was continued for about 5 hours. After the completion of the reaction, the reaction mixture was filtered to remove the catalyst. A light-brown viscous liquid was obtained.

The chemical structure and the properties of the tertiary aminoalcohol thus prepared are given in Table (Example E) Synthesis of a tertiary aminoalcohol A reaction was continued for 8 hours under the same conditions as those of the Example D except that the reaction temperature was 190° C., 1,9-nonanediol was used as the alcohol, and N,N-dimethylethylenediamine was used as the diamine.

The chemical structure and properties of the tertiary aminoalcohol thus prepared are given in Table 1.

(Example F) Synthesis of a tertiary aminoalcohol

A reaction was continued for about 15 hours under the same conditions as those of Example D except that the reaction temperature was 220° C., triethylene glycol was used as the alcohol, the amount of the catalyst used was 4% by weight based on the starting alcohol, and N,N-dibutylpropylenediamine was used as the diamine.

The chemical structure and properties of the tertiary aminoalcohol thus prepared are given in Table 1.

TABLE 1

|  | Ex. D | Ex. E | Ex. F |
| --- | --- | --- | --- |
| $-R_1-$ | $-C_6H_{12}-$ | $-C_9H_{18}-$ | $-(C_2H_4O)_2-(C_2H_4)-$ |
| $-R_2-$ | $-C_3H_6-$ | $-C_2H_4-$ | $-C_3H_6-$ |
| $-R_3$ | $-CH_3$ | $-CH_3$ | $-C_4H_9$ |
| $-R_4$ | $-CH_3$ | $-CH_3$ | $-C_4H_9$ |
| n | 2.7 | 5.6 | 2.2 |
| M. W. (VPO) | 613 | 892 | 813 |
| OHV | 162 | 148 | 185 | wherein OHV represents a hydroxyl value (KOHmg/g).

(Examples 1 to 5 and Comparative Examples 1 and 2)

The tertiary amino alcohols according to the present invention and a general-purpose polyol for comparison were examined for reactivity by the following method:

50 ml of a solution of a tertiary aminoalcohol prepared in one of Examples D to F in benzene having a concentration of 0.1533 mol/l and 50 ml of a solution of TDI-100 (2,4-toluene diisocyanate; 100%) in benzene having a concentration of 0.1533 mol/l were fed into a 200-ml Erlenmeyer flask fitted with a ground-in stopper. The flask was allowed to stand in a thermostatic chamber at 30° C. to conduct the reaction. The reaction was monitored based on the decrease in the isocyanate concentration of the reaction system. More precisely, the reaction mixture was sampled with a 10-ml pipette every hour until 4 hours after the initiation of the reaction. Each sample was added to 5 ml of a solution of n-butylamine in dioxane having a concentration of 25 g/l. The obtained mixture was sufficiently shaken and titrated with a 0.2N alcoholic solution of hydrochloric acid to determine the amount of the hydrochloric acid consumed by the titration while a blank solution (5 ml) was also titrated similarly to determine the amount of the hydrochloric acid consumed. The isocyanate concentration of the sample was determined based on the difference between these amounts.

When Y stands for an isocyanate concentration decreased by the reaction, the 1/Y value is proportional to the reaction time t. The 1/Y value after 2 hours from the initiation of the reaction is given in Table 2.

The infrared spectrum of the polyurethane obtained in Example 1 was determined. The spectrum is given in FIG. 2.

TABLE 2

|  |  |  | Ex. No. | | | | | Comp. Ex. No. | |
| --- | --- | --- | --- | --- | --- | --- | --- | --- | --- |
|  |  |  | 1 | 2 | 3 | 4 | 5 | 1 | 2 |
| Raw material (pt. by wt.) | tert. amino- alcohol | Ex. D | 100 | 50 | 10 |  |  |  |  |
|  |  | Ex. E |  |  |  | 10 |  |  |  |
|  |  | Ex. F |  |  |  |  | 100 |  |  |
|  | general- |  |  | 50 | 90 | 90 |  | 100 | 100 |

TABLE 2-continued

| Formulation | | Ex. No. 1 | 2 | 3 | 4 | 5 | Comp. Ex. No. 1 | 2 |
|---|---|---|---|---|---|---|---|---|
| purpose polyol[*1] | | | | | | | | |
| catalyst[*2] | | | | | | | | 2 |
| 1/Y | | 160 | 95 | 38 | 52 | 31 | 14 | 22 | note)
[*1] a product of Asahi Glass Co., Ltd., Excenol 2020
[*2] a product of Kao Corporation, tetramethylhexanemethylenediamine (Kaolizer No.1)

TABLE 3

| Formulation | | Comp. Ex. No. 3 | 4 | 5 | 6 | 7 | 8 | Ex. No. 6 | 7 | 8 | 9 | 10 | 11 | 12 | 13 | 14 | 15 | 16 |
|---|---|---|---|---|---|---|---|---|---|---|---|---|---|---|---|---|---|---|
| polyol A (pt. by wt.) | | 100 | 100 | 100 | 100 | 100 | 100 | 90 | 80 | 90 | 90 | 90 | 90 | 90 | 90 | 90 | 80 | 70 |
| tert. amino-alcohol (pt. by wt.) | Ex. D | | | | | | | 10 | 20 | | | 10 | 10 | 10 | 10 | 10 | | |
| | Ex. E | | | | | | | | | 10 | | | | | | | 20 | |
| | Ex. F | | | | | | | | | | 10 | | | | | | | 30 |
| foaming agent (pt. by wt.) | water | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | R-11 | 40 | | | | | | 40 | 40 | 40 | 40 | 40 | | | | | | |
| | R-123 | | 40 | | | | | | | | | | 40 | | | | | |
| | R-141b | | | 40 | | | | | | | | | | 40 | | | | |
| | R-22 | | | | 40 | | | | | | | | | | 40 | | | |
| | R-142b | | | | | 40 | | | | | | | | | | 40 | | 40 |
| | R-134a | | | | | | 40 | | | | | | | | | | 40 | |
| catalyst (pt. by wt.) | | 2 | 2 | 2 | 2 | 2 | 2 | 2 | 2 | 2 | 2 | 2 | 2 | 2 | 2 | 2 | 2 | 2 |
| free density (kg/m$^3$) | | 22.5 | 25.3 | 20.1 | 23.8 | 23.3 | 25.0 | 22.8 | 21.9 | 22.6 | 23.7 | 23.6 | 21.4 | 22.6 | 23.0 | 23.2 | 23.5 | 22.0 |
| mold filling (cm) | | 83 | 71 | 86 | 80 | 77 | 76 | 88 | 93 | 88 | 83 | 78 | 95 | 88 | 85 | 83 | 82 | 90 | that 350 g of the starting material was poured into an inverted L-shaped aluminum mold at temperature adjusted to 40° C. (cm/350 g)

The results are given in Table 3.

(Examples 6 to 16 and Comparative Examples 3 to 8)

Each formulation specified in Table 3 (the tertiary aminoalcohols prepared in Examples D to F and other components), a foam stabilizer and a polyisocyanate component were mixed with each other and the obtained mixture was evaluated for foaming properties.

The polyol A used together with the tertiary aminoalcohols is a mixture comprising 70 parts of an aromatic amine polyol (OHV: 450) (a product of Asahi Olin Ltd.), 20 parts of sugar polyether polyol (OHV: 530) (a product of Sumitomo Bayer Urethane Co., Ltd.) and 10 parts of glycerin polyether polyol, that is polyether polyol derived from glycerol, (OHV: 235) (a product of Mitsui Toatsu Chemical, Inc.). Further, 1.5 parts of L-5340 (a product of Nippon Unicar Co., Ltd.) was used as the foam stabilizer, while a mixture of tetramethylhexamethylenediamine (Kao Lizer No. 1, a product of Kao Corporation) with pentamethyldiethylenetriamine (Kao Lizer No. 3) in a weight ratio of 3:1 was used as the catalyst. Furthermore, TR-50BX (wt. % of isocyanate: 30.7, a product of Mitsui Toatsu Chemical, Inc.) was used in an NCO to OH ratio of 1.05 as the polyisocyanate component.

When chlorodifluoromethane (R-22), 1,1,1-chlorodifluoroethane (R-142b) or 1,1,1,2-tetrafluoroethane (R-134a) was used as the foaming agent, the starting materials were premixed and the obtained mixture was foamed on a high-pressure mixer.

The free density and mold filling property were determined by the following method:

① free density: density obtained when the foaming was conducted in a veneer mold having an internal dimension of 150×150×200 mm (kg/m$^3$) mold filling: length of a molded article obtained the case

[PRODUCTION OF RIGID POLYURETHANE FOAM]

(Examples 17 to 23 and Comparative Examples 9 to 11)

Starting materials for the production of a rigid polyurethane foam, i.e., each formulation specified in Table 4 and a polyisocyanate component, were mixed with each other and the obtained mixture was foamed by the conventional procedure. Specifically, polyol component(s) (the polyol A described in the Examples 6 to 16, the tertiary amino alcohol and/or glycerol), a foaming agent, a foam stabilizer, a catalyst and a polyisocyanate were mixed with each other and the obtained mixture was stirred and poured into a mold having a size of 20×20×5 cm and kept at 40° C. 10 minutes after the pouring, demolding was conducted to obtain a rigid polyurethane foam, which was used as a sample for various evaluations. When R-22, R-142b or R-134a was used as the foaming agent, the starting materials were premixed and the obtained mixture was foamed on a high-pressure foaming machine.

In this case, 1.5 parts by weight of L-5340 (a product of Nippon Unicar Co., Ltd.) was used as the foam stabilizer and in Comparative Examples 9 and 10, tetramethylhexamethylenediamine (a product of Kao Corporation, Kao Lizer No. 1) was used in an amount specified in Table 4 as the catalyst. Further, TR-50BX (wt. % of isocyanate: 30.7, a product of Mitsui Toatsu Chemical, Inc.) was used in an NCO to OH ratio of 1.05 as the polyisocyanate component. The glycerol used as a polyfunctional alcohol (polyol) is a purified one (OHV: 1830, a product of Kao Corporation).

Each rigid polyurethane foam thus produced was stored at −30° C. for 24 hours to determine the percentage dimensional change before and after the storage. Further, the above foam (before the storage) was cut into a size of 18×18×2.5 cm and was examined for thermal conductivity with a thermal conductivity meter (Anakon Model 88). In Table 4, the amount of resin breakage refers to the amount of a resin determined in the measurement of the friability as one measure of the adhesiveness by the following method. Starting materials of a rigid polyurethane foam were stirred and poured into the above-described mold kept at 40° C. 5 minutes after the pouring, demolding was conducted to determine the amount of the resin adherent to the mold, which was defined as the amount of resin breakage. The free density and mold filling were determined by the same method as that used in the Examples 6 to 16 and Comparative Examples 3 to 8. The results are given in Table 4.

17 to 23 and Comparative Examples 9 to 11. The results are given in the Table 5.

The polyol A and L-5340 described in Table 5 and polyisocyanate component used are the same as those used in Examples 17 to 23 and Comparative Examples 9 to 11. The ethylene glycol used as a polyol is a first-grade reagent (OHV: 1810) of Katayama Chemical Industry Corp., while the 1,6-hexanediamine used is also a first-grade reagent of Katayama Chemical Industry Corp.

TABLE 4

| | | | Comp. Ex. No. | | | Ex. No. | | | | | | |
|---|---|---|---|---|---|---|---|---|---|---|---|---|
| | | | 9 | 10 | 11 | 17 | 18 | 19 | 20 | 21 | 22 | 23 |
| starting material compsn. (pt. by wt.) | tert. amino- alcohol | Ex. D | | | 10 | 10 | 10 | | | 20 | | |
| | | Ex. E | | | | | | 10 | | | 20 | |
| | | Ex. F | | | | | | | 10 | | | 30 |
| | polyol A | | 100 | 90 | 90 | 80 | 80 | 80 | 80 | 70 | 70 | 60 |
| | glycerol | | | 10 | | 10 | 10 | 10 | 10 | 10 | 10 | 10 |
| | catalyst | | 2 | 2 | | | | | | | | |
| | L-5340 | | 1.5 | 1.5 | 1.5 | 1.5 | 1.5 | 1.5 | 1.5 | 1.5 | 1.5 | 1.5 |
| | water | | 1.5 | 1.5 | 1.5 | 1.5 | 1.5 | 1.5 | 1.5 | 1.5 | | |
| | R-11 | | 40 | 40 | 40 | 40 | | | | | | |
| | R-123 | | | | | | 48 | | 48 | | | |
| | R-141b | | | | | | | 35 | | | | |
| | R-22 | | | | | | | | | 30 | | |
| | R-142b | | | | | | | | | | 33 | |
| | R-134a | | | | | | | | | | | 33 |
| property of foam | free density (kg/m$^3$) | | 22.5 | 22.3 | 22.0 | 22.4 | 22.6 | 22.1 | 22.7 | 22.1 | 23.1 | 23.2 |
| | mold filling (cm) | | 83 | 77 | 88 | 80 | 99 | 80 | 80 | 85 | 86 | 78 |
| | thermal conductivity $\times 10^{-4}$ (kcal/hm °C.) | | 137 | 131 | 136 | 130 | 139 | 136 | 131 | 130 | 132 | 132 |
| | low temp. dimensional stability (%; −30° C., 24 hr) | | −0.6 | −0.1 | −0.8 | −0.1 | −0.3 | −0.2 | −0.1 | −0.1 | −0.3 | −0.3 |
| | amt. of resin breakage (g; 40° C., 5 min) | | 0.5 | 0.8 | 0.3 | 0.3 | 0.2 | 0.4 | 0.1 | 0.0 | 0.2 | 0.2 |

TABLE 5

| | | | Ex. No. | | | | | |
|---|---|---|---|---|---|---|---|---|
| | | | 24 | 25 | 26 | 27 | 28 | 29 |
| starting material compsn. (pt. by wt.) | tert. aminoalcohol | Ex. D | 10 | | | 10 | 10 | 10 |
| | | Ex. E | | 10 | | | 5 | |
| | | Ex. F | | | 15 | 10 | | |
| | polyol A | | 80 | 75 | 70 | 60 | 70 | 80 |
| | ethylene glycol | | 10 | 10 | 10 | 10 | 10 | 10 |
| | 1,6-hexanediamine | | | 5 | 5 | 10 | 5 | |
| | L-5340 | | 1.5 | 1.5 | 1.5 | 1.5 | 1.5 | 1.5 |
| | water | | 1.5 | 1.5 | 1.5 | 1.5 | 1.5 | 1.5 |
| | R-123 | | 48 | 48 | | | 48 | |
| | R-22 | | | | 15 | 15 | | 35 |
| | R-142b | | | | 20 | 20 | | |
| property of foam | free density (kg/m$^3$) | | 22.0 | 21.3 | 22.5 | 21.9 | 21.0 | 23.0 |
| | thermal conductivity $\times 10^{-4}$ (kcal/hm °C.) | | 140 | 141 | 144 | 143 | 142 | 143 |
| | low temp. dimensional stability (%; −30° C., 24hr) | | −0.3 | −0.1 | −0.3 | −0.3 | −0.4 | −0.4 |
| | amt. of resin breakage (g; 40%, 5 min) | | 0.2 | 0.4 | 0.3 | 0.3 | 0.3 | 0.3 |

(Examples 24 to 29)

Starting materials for the production of a rigid polyurethane foam, i.e., each formulation specified in Table 5 and a polyisocyanate component, were mixed with each other and the obtained mixture was foamed in the same method as that described above to give a rigid polyurethane foam. Each of the rigid polyurethane foams thus produced was used as the sample for various evaluations. When R-22 or R-142b was used as a foaming agent, the starting materials were premixed in a 20-l premixing tank with static mixer and foamed on a high-pressure mixer. The samples thus prepared were each examined for free density, thermal conductivity, low-temperature dimensional stability and amount of resin breakage in the same method as described in Examples

[PRODUCTION OF RIGID POLYURETHANE FOAM BY SPRAY METHOD]

(Comparative Examples 12 and 13)

Foaming was conducted by the following method according to each of the conventional formulations for spray type rigid polyurethane foam as specified in Table 6.

Specifically, the starting materials listed in Table 6 except for Crude MDI were preliminarily mixed with each other and the obtained mixture was kept at 5° C. Crude MDI adjusted to a temperature of 5° C. was reacted with a predetermined amount of the above mixture by hand mixing foaming to determine the reaction rate (cream time, gel time and rise time) and the physical and mechanical properties of the resultant foams.

In this specification, the term "cream time (CT)" refers to a time taken from the initiation of the mixing and/or stirring of Crude MDI with the above mixture to the initiation of the foaming; the term "gel time (GT)" refers to a time taken until the resultant resin elongates in stringy form when a tip of a sharp-edged material is brought into contact with the surface of the polyurethane foam and then separated therefrom; and the term "rise time (RT)" refers to a time taken until the polyurethane foam reaches its largest volume.

The self adhesive bonding strength was determined according to the method prescribed in JIS A 9526. Specifically, a sample was prepared by preliminarily mixing starting materials except for Crude MDI with each other and maintaining the mixture at 5° C. Crude MDI adjusted to a temperature of 5° C. was reacted with a predetermined amount of the above sample by hand mixing, applying the liquid mixture to a veneer kept at 5° C. by spraying, and foaming and curing the resulting coating. The environmental temperature during the foaming was maintained at 5° C. Other properties of the polyurethane foam were evaluated according to the method prescribed in JIS A 9526. The results are given in Table 7.

(Examples 30 to 33)

Foaming was conducted according to each formulation specified in Table 6 wherein the tertiary aminoalcohols prepared in Examples D and E was used in the same method as that of Comparative Example 12 and the obtained foams were each examined for various properties.

The results are given in Table 7.

(Example 34 and Comparative Example 14)

A foaming test at a low temperature (0° C.) was conducted according to each of the formulations specified in the columns of Example 34 and Comparative Example 14 in Table 6. The foaming was conducted under the same conditions as those of Comparative Examples 12 and 13 and Examples 30 to 33, except that the temperature of the starting materials was kept at 0° C. Further, the temperature of the sample for the self adhesive bonding strength test and the room temperature during the test were kept at 0° C. The results are given in Table 7.

TABLE 6

|  | Ex. No. | | | | | Comp. Ex. No. | | |
| --- | --- | --- | --- | --- | --- | --- | --- | --- |
|  | 30 | 31 | 32 | 33 | 34 | 12 | 13 | 14 |
| general-purpose polyol B | 24 pts. | ← | ← | ← | ← | 30 | ← | ← |

TABLE 6-continued

|  | Ex. No. | | | | | Comp. Ex. No. | | |
| --- | --- | --- | --- | --- | --- | --- | --- | --- |
|  | 30 | 31 | 32 | 33 | 34 | 12 | 13 | 14 |
| general-purpose polyol C | 56 | ← | ← | ← | ← | 70 | ← | ← |
| tert. amino-alcohol (Ex. D) | 20 | ← | 0 | ← | 20 | 0 | ← | ← |
| tert. amino-alcohol (Ex. E) | 0 | ← | 20 | ← | 0 | 0 | ← | ← |
| amine catalyst (Kao Lizer No. 1) | 2 | ← | ← | ← | ← | 2 | ← | ← |
| metal catalyst (lead octanoate, Pb: 25%) | 0.5 | ← | ← | ← | ← | 0.5 | ← | ← |
| water | 3 | 6 | 3 | 6 | 3 | 3 | 6 | 3 |
| silicone foam stabilizer | 1 | ← | ← | ← | ← | 1 | ← | ← |
| R-11 | 30 | 10 | 30 | 10 | 30 | 30 | 10 | 30 |
| Crude MDI (NCO: 31%) | index 105 | ← | ← | ← | ← | ← | ← | ← |

Note: general-purpose polyol B: amine polyether polyol (OHV : 450)
general-purpose polyol C: sucrose polyether polyol (OHV : 450)

TABLE 7

|  |  | Ex. No. | | | | | Comp. Ex. No. | | |
| --- | --- | --- | --- | --- | --- | --- | --- | --- | --- |
|  |  | 30 | 31 | 32 | 33 | 34 | 12 | 13 | 14 |
| reaction temp. (°C.) | | 5 | ← | ← | ← | 0 | 5 | ← | 0 |
| reactivity | CT (sec) | 4 | 3 | 4 | 3 | 5 | 5 | 4 | 6 |
|  | GT (sec) | 13 | 11 | 12 | 10 | 15 | 14 | 13 | 18 |
|  | RT (sec) | 16 | 14 | 15 | 12 | 18 | 17 | 15 | 21 |
| foam density (g/l) | | 24.1 | 23.8 | 24.1 | 24.3 | 24.5 | 24.1 | 24.3 | 24.7 |
| self-bonding strength (kg·f/cm$^2$) | | 1.7 | 1.6 | 1.6 | 1.6 | 1.5 | 1.5 | 1.3 | 1.2 |
| compressive strength (kg/cm$^2$) | | 1.0 | 0.9 | 0.9 | 1.0 | 0.9 | 0.8 | 0.7 | 0.7 |

[PRODUCTION OF FLEXIBLE POLYURETHANE FOAM]

(Examples 35 to 37)

According to each formulation specified in Table 8, polyether polyol derived from glycerol, the tertiary amino alcohol prepared in Examples D and E, water and a silicone foam stabilizer were preliminarily mixed with each other and the temperature of the mixture was adjusted to 25° C..

Then, stannous octanoate was added thereto and the obtained mixture was stirred for 5 seconds. TDI-80 (2,4-tolylene diisocyanate/2,6-tolylene diisocyanate: 80/20 by mole) adjusted to a temperature of 25° C. was immediately added to the resulting mixture and the obtained mixture was further stirred for 5 seconds and poured into an aluminum mold having a size of 30×30×7 cm kept at 60° C.. The mold was placed in an oven set at 160° C., and curing was conducted for 10 minutes to give a flexible mold polyurethane foam.

The physical properties of the foams thus produced were evaluated according to the method prescribed in JIS A 6402. The results are given in Table 8.

(Comparative Example 15)

According to the formulation specified in Table 8, foaming was conducted under the same conditions as those of Examples 35 to 37, except that polyether polyol derived from glycerol alone was used as a polyol and that catalyst (KL-31 and KL-21) were used instead of the tertiary aminoalcohol. The obtained foam was evaluated for physical properties in the same method as described in Examples 35 to 37. The results are given in Table 8.

TABLE 8

|  |  | Ex. 35 | Ex. 36 | Ex. 37 | Comp. Ex. 15 |
|---|---|---|---|---|---|
| formulation (g) | polyether polyol derived from glycerol (OHV:56) | 142.5 | 145.5 | 142.5 | 150 |
|  | tert. aminoalcohol (Ex. D) | 7.5 | 4.5 | — | — |
|  | tert. aminoalcohol (Ex. E) | — | — | 7.5 | — |
|  | water | 6.8 | 6.8 | 6.8 | 6.8 |
|  | silicone foam stabilizer | 2.3 | 1.5 | 2.3 | 1.5 |
|  | stannous octanoate | 0.1 | 0.1 | 0.1 | 0.1 |
|  | KL-31*[1] | — | — | — | 0.4 |
|  | KL-21*[2] | — | — | — | 0.4 |
|  | TDI-80*[3] | index 100 | index 100 | index 100 | index 100 |
| mold temp. during pouring (°C.) |  | 60 | 60 | 60 | 60 |
| state of foam | surface | good | good | good | peeling |
|  | inside | good | good | good | cracking |
| properties of foam | overall density (g/l) | 29.0 | 29.2 | 28.7 | 32.2 |
|  | hardness (F type) | 65 | 61 | 64 | 67 |
|  | tensile strength (kg/cm$^2$) | 1.60 | 1.56 | 1.54 | 1.52 |
|  | tear strength (kg/cm$^2$) | 0.73 | 0.76 | 0.74 | 0.75 |
|  | elongation (%) | 152 | 150 | 161 | 155 |
|  | permanent compression set (50%, 70° C. × 22 hr) | 4.7 | 4.6 | 4.5 | 4.5 |
|  | gas permeability (cc/cm$^2$/sec) | 17.1 | 16.6 | 16.9 | 11.6 |

Note)
*[1] 33% solution of triethylenediamine in dipropylene glycol
*[2] N-ethylmorpholine
*[3] tolylene diisocyanate (2,4-/2,6-isomer = 80/20)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim:

1. A process for producing a polyurethane comprising a step of reacting a polyisocyanate component with a polyol component, wherein a tertiary aminoalcohol represented by the following general formula (I) is used as at least part of the polyol component:

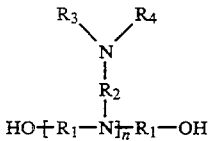
(I)

wherein $R_1$ each represents a straight-chain or branched alkylene group having 2 to 24 carbon atoms, a cycloalkylene group having 3 to 24 carbon atoms, a cycloalkyl alkylene group having 4 to 24 carbon atoms, an arylene group having 6 to 24 carbon atoms, an aralkylene group having 7 to 24 carbon atoms or $-(CH_2CH_2O)_p-(CH_2CH_2)_q-$ (p being 0 or a positive number and q being a positive number), $R_2$ each represents a straight-chain or branched alkylene group having 1 to 9 carbon atoms, $R_3$ each represents a straight-chain or branched alkyl group having 1 to 4 carbon atoms, $R_4$ each represents a straight-chain or branched alkyl group having 1 to 4 carbon atoms and n, which is an average polymerization degree, represents a positive number of 2 to 50.

2. The process according to claim 1, wherein in the general formula (I), $R_1$ each represents a straight-chain or branched alkylene group having 3 to 9 carbon atoms, $R_2$ each represents a straight-chain or branched alkylene group having 1 to 3 carbon atoms, $R_3$ each represents a straight-chain or branched alkyl group having 1 to 4 carbon atoms, $R_4$ each represents a straight-chain or branched alkyl group having 1 to 4 carbon atoms and n represents a positive number of 2 to 10.

3. A process for producing a polyurethane comprising a step of reacting a polyisocyanate component with a polyol component, wherein a tertiary aminoalcohol represented by the following general formula (III) is used as at least part of the polyol component:

wherein $R_1$ represents a straight-chain or branched alkylene group having 2 to 24 carbon atoms, an alicyclic alkylene group having 2 to 24 carbon atoms, an aralkylene group having 2 to 24 carbon atoms or a $-(CH_2CH_2O)_p-(CH_2CH_2)_q-$ group (p being 0 or a positive number and q being a positive number);

$R_2$ represents a straight-chain or branched alkylene group having 1 to 9 carbon atoms;

$R_3$ and $R_4$ each represent a straight-chain or branched alkyl group having 1 to 4 carbon atoms;

and n is a positive number of 2 to 50.

4. A polyurethane produced by the process as claimed in claim 1.

5. A process for producing a polyurethane foam comprising a step of reacting a polyisocyanate component with a polyol component coexisting of a foaming agent, wherein a tertiary aminoalcohol represented by the following general formula (I) is used as at least part of the polyol component:

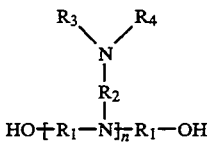

wherein $R_1$ each represents a straight-chain or branched alkylene group having 2 to 24 carbon atoms, a cycloalkylene group having 3 to 24 carbon atoms, a cycloalkyl alkylene group having 4 to 24 carbon atoms, an arylene group having 6 to 24 carbon atoms, an aralkylene group having 7 to 24 carbon atoms or $-(CH_2CH_2O)_p-(CH_2CH_2)_q-$ (p being 0 or a positive number and q being a positive number), $R_2$ each represents a straight-chain or branched alkylene group having 1 to 9 carbon atoms, $R_3$ each represents a straight-chain or branched alkyl group having 1 to 4 carbon atoms, $R_4$ each represents a straight-chain or branched alkyl group having 1 to 4 carbon atoms and n, which is an average polymerization degree, represents a positive number of 2 to 50.

6. The process according to claim 5, wherein the polyol component includes 1 to 50% by weight of the tertiary aminoalcohol represented by the general formula (I).

7. The process according to claim 5, wherein at least one compound selected from the group consisting of aliphatic amines and aromatic amines is used in the step of reacting a polyisocyanate component with the polyol component.

8. The process according to claim 5, wherein at least one compound selected from the group consisting of triethanolamine, tolylenediamine and a diamine compound represents by general formula (V):

, $H_2N-R_5-NH_2$ (V)

wherein $R_5$ represents a straight-chain or branched alkylene group having 2 to 8 carbon atoms, is used in the step of reacting a polyisocyanate component with the polyol component.

9. The process according to claim 7, wherein the amount of the compound selected from the group consisting of aliphatic amines and aromatic amines is 1 to 30 parts by weight based on 100 parts by weight of the total amount of the polyol component.

10. The process according to claim 5, wherein the foaming agent is at least one compound selected from the group consisting of $H_2O$, 1,1-dichloro-2,2,2-trifluoroethane, 2,2-dichloro-2-fluoroethane, chlorodifluoromethane, 1,1,1-chlorodifluoroethane and 1,1,1,2-tetrafluoroethane.

11. The process according to claim 5, wherein the polyurethane foam is a rigid polyurethane foam.

12. The process according to claim 11, wherein the polyol component includes a polyol having the OH value being 1000 and above.

13. The process according to claim 11, wherein the polyol component includes ethyleneglycol and/or glycerol each having the OH value being 1000 and above.

14. The process according to claim 11, wherein an average OH value of the polyol component is 300 and above.

15. The process according to claim 5, wherein the polyurethane foam is a flexible polyurethane foam.

16. The process according to claim 15, wherein an average OH value of the polyol component is 200 and below.

17. The process according to claim 15, wherein the foaming agent is $H_2O$ and the foaming agent is used in amount of 2 to 8 parts by weight based on 100 parts by weight of the total amount of the polyol component.

18. A process for producing a polyurethane foam by spray method comprising steps of spraying a mixture comprising a polyisocyanate component, a polyol component and a foaming agent and reacting the polyisocyanate component with the polyol component coexisting of the foaming agent, wherein a tertiary aminoalcohol represented by the following general formula (I) is used as at least part of the polyol component:

wherein $R_1$ each represents a straight-chain or branched alkylene group having 2 to 24 carbon atoms, a cycloalkylene group having 3 to 24 carbon atoms, a cycloalkyl alkylene group having 4 to 24 carbon atoms, an arylene group having 6 to 24 carbon atoms, an aralkylene group having 7 to 24 carbon atoms or $-(CH_2CH_2O)_p-(CH_2CH_2)_q-$ (p being 0 or a positive number and q being a positive number), $R_2$ each represents a straight-chain or branched alkylene group having 1 to 9 carbon atoms, $R_3$ each represents a straight-chain or branched alkyl group having 1 to 4 carbon atoms, $R_4$ each represents a straight-chain or branched alkyl group having 1 to 4 carbon atoms and n, which is an average polymerization degree, represents a positive number of 2 to 50, and $H_2O$ is used as the foaming agent in amount of 2 to 8 parts by weight based on 100 parts by weight of the total amount of the polyol component.

19. The process according to claim 18, wherein the polyol component includes 1 to 50% by weight of the tertiary aminoalcohol represented by the general formula (I).

20. The process according to claim 18, wherein the polyurethane foam is a rigid polyurethane foam.

* * * * *